(12) United States Patent
Blake (10) Patent No.: US 7,435,258 B2
(45) Date of Patent: Oct. 14, 2008

(54) ACCOMMODATING INTRAOCULAR LENS DEVICE

(76) Inventor: Larry W. Blake, 31082 Via Caza, Coto de Caza, CA (US) 92679

( * ) Notice: Subject to any disclaimer, the term of this patent is extended or adjusted under 35 U.S.C. 154(b) by 487 days.

(21) Appl. No.: 10/942,992

(22) Filed: Sep. 17, 2004

(65) Prior Publication Data
US 2006/0064161 A1 Mar. 23, 2006

(51) Int. Cl.
*A61F 2/16* (2006.01)
(52) U.S. Cl. .................. 623/6.37; 623/6.4; 623/6.44
(58) Field of Classification Search ............... 623/6.37, 623/6.4–6.42, 6.44, 6.46, 6.38, 6.39, 6.43
See application file for complete search history.

(56) References Cited

U.S. PATENT DOCUMENTS

| 4,441,217 | A  | * | 4/1984  | Cozean, Jr. ............ 623/6.43 |
| 6,616,691 | B1 | * | 9/2003  | Tran ....................... 623/6.11 |
| 6,932,839 | B1 | * | 8/2005  | Kamerling et al. ........ 623/6.24 |
| 7,025,783 | B2 | * | 4/2006  | Brady et al. ............... 623/6.22 |
| 2004/0236423 | A1 |   | 11/2004 | Zhang et al. |

FOREIGN PATENT DOCUMENTS

FR    2 832 920 A1 *  6/2003

OTHER PUBLICATIONS

EPO machine translation of FR 2 832 920 A1 (9 pages).*

* cited by examiner

*Primary Examiner*—Dave Willse
(74) *Attorney, Agent, or Firm*—William L. Klima; Klima Law Offices, PLLC (57) ABSTRACT

An accommodating intraocular lens device including a lens portion connected to a plate haptic portion. Preferably, the lens portion is connected to the plate haptic portion by a pair of flexible or resilient arms.

25 Claims, 5 Drawing Sheets

ACCOMMODATING INTRAOCULAR LENS DEVICE

FIELD OF THE INVENTION

The present invention is directed to an accommodating intraocular lens device, preferably for use in the capsular bag after cataract lens removal.

BACKGROUND OF THE INVENTION

Currently, there exists a high level of cataract lens surgeries performed in the United States and in other countries and territories throughout the world. These cataract lens surgeries involve the removal of the natural lens, typically by phacoemulsification, followed by the implantation of an intraocular lens (IOL).

Most cataract lens surgeries are performed using an intraocular lens providing little if any accommodation of the eye. Specifically, the intraocular lens is implanted into the capsular bag of the eye, and once healing of the eye has occurred, there is very little movement of the intraocular lens in a manner to focus the eye by accommodation like the natural crystalline lens of the eye.

There has been much interest in creating and designing intraocular lens configured to provide accommodation the same or similar to the natural crystalline lens of the eye. It is believed that the next generation of intraocular lenses will be accommodating intraocular lenses that provide a significant amount of accommodation of at least one (1) diopter or more. So far, most accommodating intraocular lenses being clinically studied provide one (1) dioper or less of accommodation of the eye. Thus, there now exists a need for an accommodating intraocular lens that can provide a substantial amount of accommodation of the eye, desirably, providing one (1) or more diopters of accommodation of the eye.

The present invention is directed to an accommodating intraocular lens configured in a manner that may provide for substantial accommodation of the eye.

SUMMARY OF THE INVENTION

A first object of the present invention is to provide an improved accommodating intraocular lens.

A second object of the present invention is to provide an accommodating intraocular lens including a lens portion flexibly or resiliently connected to a plate haptic portion.

A third object of the present invention is to provide an accommodating intraocular lens including a lens portion connected to a plate haptic portion by at least by one flexible arm.

A fourth object of the present invention is to provide an accommodating intraocular lens including a lens portion connected to a plate haptic portion and configured to move the lens portion relative to the plate haptic portion when force is applied to the edge of the plate haptic portion.

A fifth object of the present invention is to provide an accommodating intraocular lens including a lens portion connected to a plate haptic portion, the lens portion being separate and spaced apart from the plate haptic portion by a predetermined distance, the lens portion and the haptic portion being connected together by at least one flexible or resilient arm.

The present invention is directed to an improved accommodating intraocular lens.

The accommodating intraocular lens according to the present invention includes a lens portion connected to a haptic portion, preferably a plate haptic portion. The lens portion can be a hard intraocular lens (e.g. made of polymethylmethacrylate (PMMA) or a deformable or resilient intraocular lens (e.g. made of silicon, collagen based polymer, polymethyl methacrylate (PMMA), acrylic polymer, polyamide, polyester, polysulfone, polyethersulfone and other biological compatible materials of suitable refractive index. The plate haptic portion is preferably made of a substantial flexible or resilient material and configured to allow the plate haptic to bow when an inwardly directed force is applied to the edges or edge portions of the plate hapic portion. The accommodating intraocular lens according to the present invention can be made as a single piece lens (e.g. by molding or machining), or can be a multiple-piece lens assembled together (e.g. hard or soft lens portion and resilient or deformable plate haptic portion).

Preferably, the lens portion of the accommodating intraocular lens device according to the present invention remains substantially fixed in shape and size after implantation. Specifically, it is preferred that the lens portion remains in the same conformation, and is not bent or bowed once implanted in the eye. Otherwise, the lens portion may not provide consistent light refraction during use or while the accommodating intraocular lens device is performing accommodation within the eye. However, it is to be noted that the lens portion, in particular for a deformable type accommodating intraocular lens according to the present invention, can be substantially deformed, rolled or folded during small incision insertion and implantation of the lens device into the eye.

The accommodating intraocular lens according to the present invention includes a lens portion and a haptic portion preferably a plate haptic portion. The lens portion is essentially a separate component from the haptic portion except for at least flexible or resilient arm connecting the lens portion to the haptic portion. Preferably, at least one opening is provided between an outer edge of the lens portion and an inner edge of the plate haptic portion. More specifically, the lens portion is separated from the plate haptic portion by a predetermined distance. In this arrangement, the outer edge of the lens portion is able to move substantially freely and independently relative to the inner edge of the plate haptic portion except at the point or points of connection with the flexible or resilient arm(s).

The accommodating intraocular lens according to the present invention includes at least one arm, preferably a flexible or resilient arm connecting the lens portion to the plate haptic portion. The flexible or resilient arm is configured to move the lens portion along the central focus axis of the eye when the plate haptic portion is bowed, for example, when the eye exerts an inward radial force at one or more positions around the outer edge of the plate haptic portion. More specifically, the lens portion is moved along the central focal axis of the eye for purposes of accommodation for focusing the eye when the plate haptic portion is bowed. At least one flexible arm allows the outer edge of the lens portion to move relative to the inner edge of the plate haptic portion, which becomes distorted as the plate haptic portion is bowed. In this manner, the at least one flexible or resilient arm accommodates tensile stress, shear stress and some torsional stress when the plate haptic portion is bowed without breaking or permanently deforming. Specifically, the stresses are at a level within the at least one flexible or resilient arm when the plate haptic portion is bowed so as to not cause plastic deformation of the at least one flexible or resilient arm. Thus, when the force on the outer edge of the plate haptic portion is relieved, the stresses within the at least one arm are relieved and causes the lens portion to move back to a resting position relative to the eye.

In preferred embodiments, the lens portion is initially located in the same plane as the plate haptic portion. When force is applied to the outer edge of the plate haptic portion, the plate haptic portion begins to bow and moves the lens portion out of the initial reference plane along the central focal axis of the eye. As the plate haptic portion bows, it changes shape from substantially from a two (2) dimensional configuration to a cupped or bowed three (3) dimensional configuration, and is substantially no longer planar.

The outer periphery or edge portion of the plate haptic portion is preferably configured and/or treated to facilitate or enhance anchoring thereof within the eye. Specifically, the plate haptic portion can be provided with one or more through holes to allow tissue on either side of the plate haptic portion to adhere together in the through hole. Alternatively, or in addition, the outer edge of the plate haptic portion can be provided with scallops, serrations and/or notches to facilitate tissue adherence thereto.

In preferred embodiments of the accommodating intraocular lens according to the present invention, the lens portion is circular shaped or substantially rectangular shaped. Further, preferably, the lens portion is centered relative to the shape of the outer peripheral of the plate haptic portion.

As an alternative embodiment, the lens portion can be located off centered in one or both the length and width dimensions relative to the outer perimeter of the plate haptic portion. In this manner the accommodating intraocular lens device can be customized to take into account the morphology of the interior of the eye of a particular patient in custom designing and prescribing the particular accommodating intraocular lens device for said patient.

As further alternative embodiment, an embodiments of the accommodating intraocular lens according to the present invention having a pair of flexible or resilient arms connecting the lens portion to the plate haptic portion, the lengths of the arm portions can be the same or different. Further, the location of the pair of arm portions can be located along a center axis of the lens portion or can be located off axis.

DETAILED DESCRIPTION OF PREFERRED EMBODIMENTS

A preferred embodiment of a deformable accommodating intraocular lens device 10 according to the present invention is shown in FIGS. 1 to 4.

Figure 2:
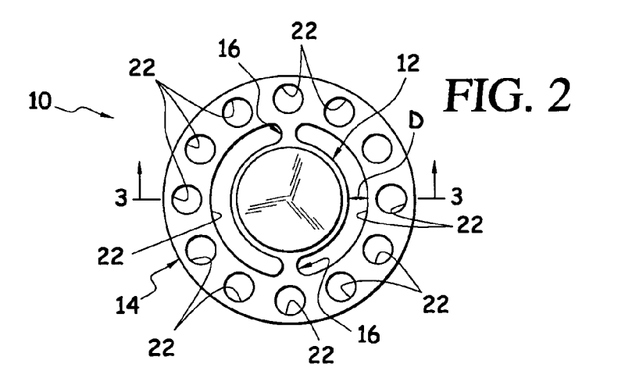
FIG. 2 is a top planar view of the deformable accommodating intraocular lens device, as shown in FIG. 1.
Figure 3:
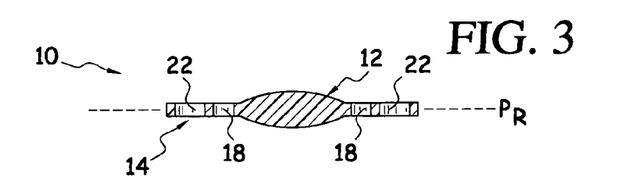
FIG. 3 is a cross-sectional view of the deformable accommodating intraocular lens device, as indicated in FIG. 2, in an unstressed condition.
Figure 4:
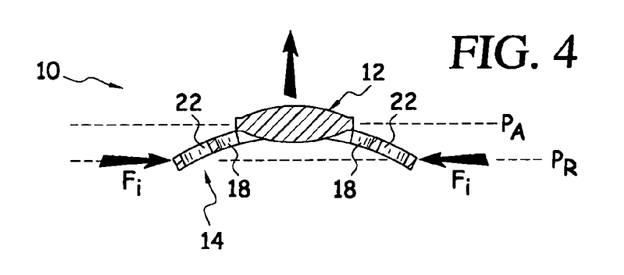
FIG. 4 is a cross-sectional view, as shown in FIG. 3, when the lens device is in a stressed condition.

The deformable accommodating intraocular lens device 10 includes a lens portion 12 and a plate haptic portion 14. The lens portion 12 is connected to the plate haptic portion 14 by a pair of flexible or resilient arm portions 16, 16, as shown in FIG. 2. A pair of partial circular-shaped openings 18, 18 separate the lens portion 12 from the plate haptic portion 14, as shown in FIG. 2, by a predetermined distance D. In this manner, the lens portion 12 is structurally substantially independent of plate haptic portion 18, except at the two (2) points of connection provided by the resilient or flexible arm portion 16, 16.

Figure 1:
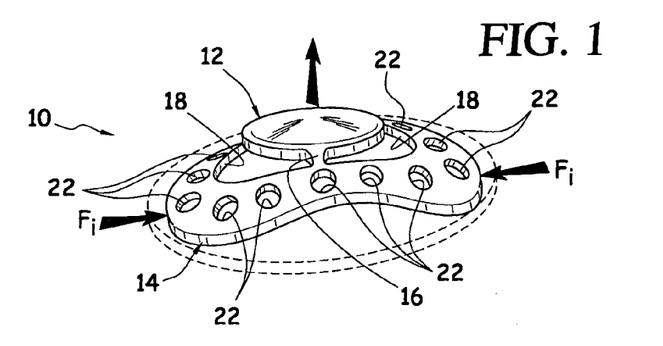
FIG. 1 is a perspective view of a deformable accommodating intraocular lens device according to the present invention shown under a stressed condition providing forward accommodation of the lens portion along the center focal axis of the eye.

The perimeter of the plate haptic portion 14 is provided with a plurality of through holes 22 to facilitate adherence of tissue looped through the through holes 22 by tissue located on either side of the perimeter of the plate haptic portion 14 connecting together in the through holes 22. In this manner, once the deformable accommodating intraocular lens device 12 has been implanted and the eye has healed, the perimeter of the plate haptic portion 14 becomes substantially anchored in place.

In the preferred embodiments shown in FIGS. 1 to 4, the lens portion 14, plate haptic portion 14 and arm portions 16, 16 are made as a one-piece unitary structure from soft, deformable or resilient polymer material. The deformable accommodating intraocular lens device 10 can be inserted through a small incision (e.g. less than 2.5 millimeters) through the cornea of the eye in a deformed rolled, folded or otherwise compressed condition by use of forceps or a lens injecting device.

Figure 5:
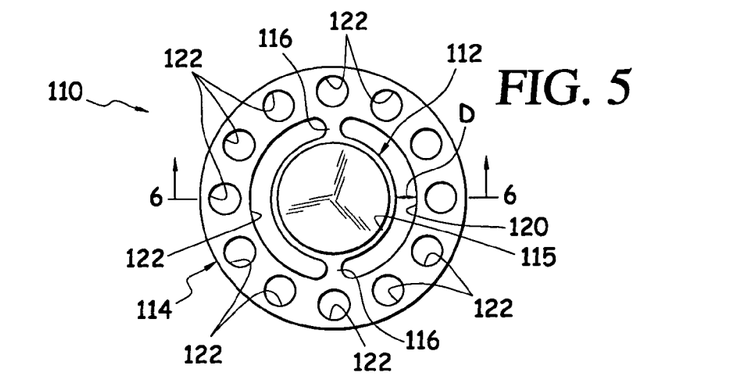
FIG. 5 is a top planar view of another embodiment of the accommodating intraocular lens device according to the present invention.
Figure 6:
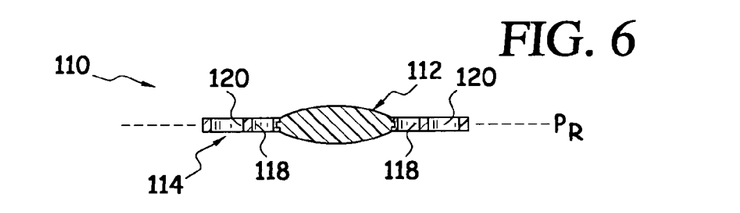
FIG. 6 is a cross-sectional view of the accommodating intraocular lens device as indicated in FIG. 5.
Figure 7:
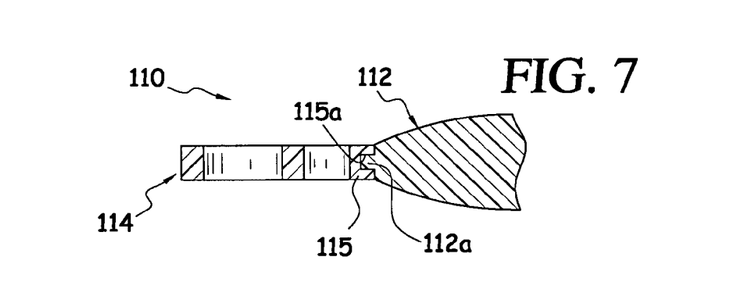
FIG. 7 is a partial broken away detailed cross-sectional view of a portion of the accommodating intraocular lens device shown in FIGS. 5 and 6.

Another embodiment of a partially deformable accommodating intraocular lens 110 device is shown in FIGS. 5-7.

The partially deformable accommodating intraocular lens device 110 includes a lens portion 112 and a plate haptic portion 114. The lens portion 112 is connected to the plate haptic portion 114 by a pair of resilient or flexible arm portions 116.

In this embodiment, the lens portion 112 is made out of non-resilient or non-deformable material such as polymethyl methacrylate. However, the plate haptic portion 114 is made from a resilient polymer material and the partially deformable accommodating intraocular lens 110 is made from two (2) separate pieces and assembled together to become a single piece lens. Further, the accommodating lens according to the present invention can be made of a material that varies in hardness or stiffness along its length (e.g. harder lens portion and softer plate haptic portions or reverse).

The plate haptic portion 114 includes a resilient lens carrier or lens receiving portion 115 provided with an inner groove 115a cooperating with a tongue portion 112a of the lens portions 112 as shown in FIG. 7. The lens portion 112 can be secured in place due to the resilient nature of the lens receiver or lens carrier 115 of the plate haptic portion 114 due to its capacity to withstand a certain amount of band stress. Alternatively, or in addition, the tongue portion 112a can be adhered by glue, adhesive, welding or other technique to secure the lens portion 112 to the lens receiver or lens carrier 115 of the plate haptic portion 114.

The partially deformable accommodating intraocular lens device is inserted through a relatively large incision in the cornea by forceps and then implanted into the capsular bag after cataract lens removal.

Figure 8:
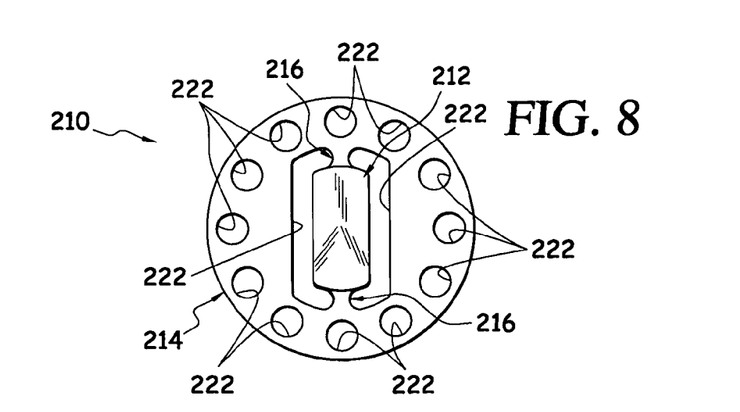
FIG. 8 is a top planar view of another embodiment of an accommodating intraocular lens according to the present invention.

A further embodiment of the accommodating intraocular lens 210 according to the present invention is shown in FIG. 8.

The accommodating intraocular lens 210 includes a substantially rectangular lens portion 212 connected to a round-shaped plate haptic portion 214 by a pair of flexible or resilient arm portions 216, 216. A pair of oblong or partial oval-shaped openings 220, 220 are provided between the lens portion 212 and the plate haptic portion 214. A plurality of through holes 222 are provided to facilitate anchoring of the perimeter of the plate haptic portion 214.

Figure 9:
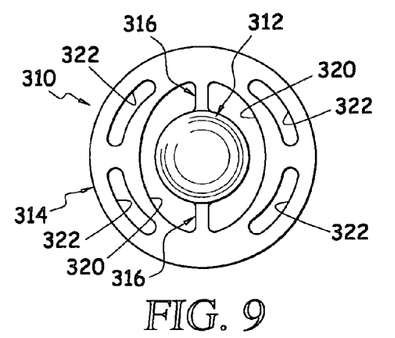
FIG. 9 is a top planar view of another embodiment of the accommodating intraocular lens according to the present invention.

A further embodiment of the accommodating intraocular lens 310 according to the present invention is shown in FIG. 9.

The accommodating intraocular lens 310 includes a substantially round lens portion 312 connected to a round plate haptic portion 314 by a pair of flexible or resilient arm portions 316, 316. A pair of oblong or partial oval-shaped openings 320, 320 are provided between the lens portion 312 and the plate haptic portion 314. A plurality of through holes 322 are provided to facilitate anchoring of the perimeter of the plate haptic portion 314.

Figure 10:
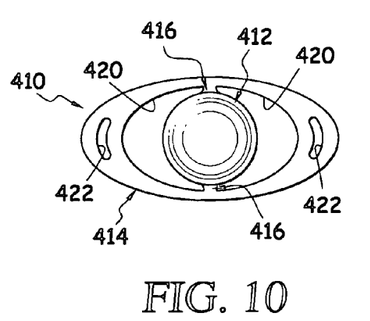
FIG. 10 is a top planar view of another embodiment of the accommodating intraocular lens according to the present invention.

A further embodiment of the accommodating intraocular lens 410 according to the present invention is shown in FIG. 10.

The accommodating intraocular lens 410 includes a substantially round lens portion 412 connected to an oblong-shape plate haptic portion 414 by a pair of flexible or resilient arm portions 416, 416. A pair of oblong or partial oval-shaped openings 420, 420 are provided between the lens portion 412 and the plate haptic portion 414. A plurality of through holes 422 are provided to facilitate anchoring of the perimeter of the plate haptic portion 414.

Figures 11, 12:
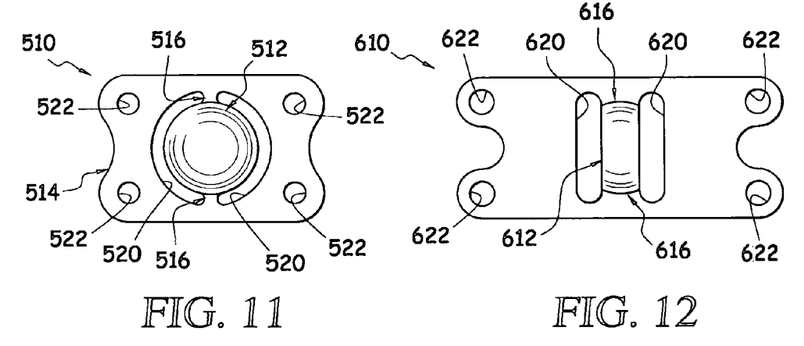
FIG. 11 is a top planar view of another embodiment of the accommodating intraocular lens according to the present invention.
FIG. 12 is a top planar view of another embodiment of the accommodating intraocular lens according to the present invention.

A further embodiment of the accommodating intraocular lens 510 according to the present invention is shown in FIG. 11.

The accommodating intraocular lens 510 includes round lens portion 512 connected to a modified oblong-shape plate haptic portion 514 by a pair of flexible or resilient arm portions 516, 516. A pair of oblong or partial oval-shaped openings 520, 520 are provided between the lens portion 512 and the plate haptic portion 514. A plurality of through holes 522 are provided to facilitate anchoring of the perimeter of the plate haptic portion 514.

Another embodiment of the accommodating intraocular lens 610 according to the present invention is shown in FIG. 12.

The accommodating intraocular lens 610 includes an elongated lens portion 612 connected to an elongated plate haptic portion 614 by a pair of flexible or resilient arm portions 616, 616. A pair of oblong-shaped openings 620, 620 are provided between the lens portion 612 and the plate haptic portion 614. A plurality of through holes 622 are provided to facilitate anchoring of the ends of the plate haptic portion 614 in the eye.

Figure 13:
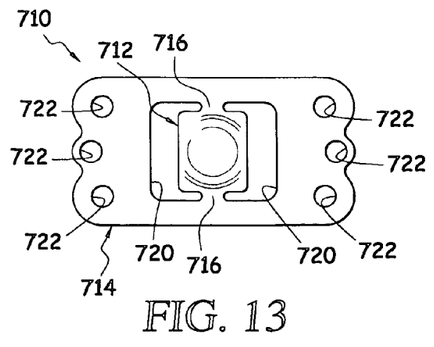
FIG. 13 is a top planar view of another embodiment of an accommodating intraocular lens according to the present invention.

A further embodiment of the accommodating intraocular lens according to the present invention is shown in FIG. 13.

The accommodating intraocular lens 710 includes a rectangular lens portion 712 connected to a rectangular plate haptic portion 714 by a pair of flexible or resilient arm portions 716, 716. A pair of rectangular oval-shaped openings 720, 720 are provided between the lens portion 712 and the plate haptic portion 714. A plurality of through holes 722 are provided to facilitate anchoring of the ends of the plate haptic portion 714 in the eye.

Figure 14:
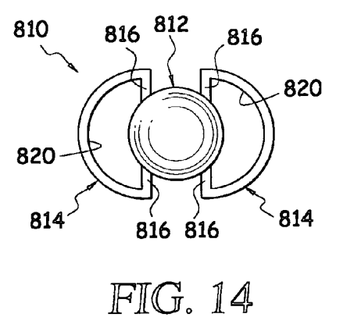
FIG. 14 is a top planar view of another embodiment of the accommodating intraocular lens according to the present invention.

An even further embodiment of the accommodating intraocular lens 810 according to the present invention is shown in FIG. 14.

The accommodating intraocular lens 810 includes a round lens portion 812 connected to a pair of half-circle plate haptic portions 814, 814 each by a pair of flexible or resilient arm portions 816, 816. A pair of half-circle shaped openings 820, 820 are provided between the lens portion 812 and the plate haptic portions 814, 814. In this embodiment, the openings 820, 820 also provide the function of through holes in previous embodiments to facilitate anchoring the ends of the plate haptic portions 814, 814 in the eye.

Figure 15:
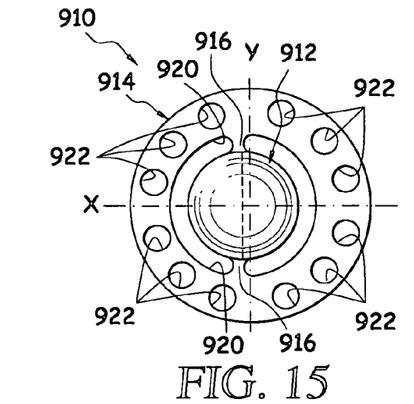
FIG. 15 is a top planar view of a further embodiment of the accommodating intraocular lens according to the present invention.

Another embodiment of the accommodating intraocular lens 910 according to the present invention is shown FIG. 15.

The accommodating intraocular lens 910 includes a round lens portion 912 connected to a round plate haptic portion 914 by a pair of flexible or resilient arm portions 916, 916. The arm portions 916, 916 are approximately the same length. A pair of half circular-shaped openings 920, 920 are provided between the lens portion 912 and the plate haptic portion 914. A plurality of through holes 922 are provided to facilitate anchoring the plate haptic portion 914 in the eye. In this embodiment, the lens portion 912 is located off centered along the Y axis making the round plate haptic portion somewhat asymmetrical in shape relative to the X axis.

Figure 16:
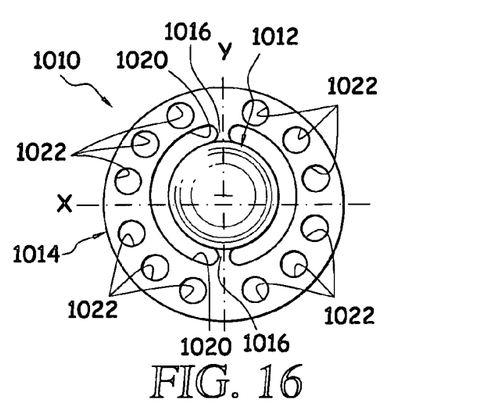
FIG. 16 is a top planar view of a further embodiment of the accommodating intraocular lens according to the present invention.

Another embodiment of the accommodating intraocular lens 1010 according to the present invention is shown in FIG. 16.

The accommodating intraocular lens 1010 includes a round lens portion 1012 connected to a round plate haptic portion 1014 by a pair of flexible or resilient arm portions 1016, 1016. A pair of half circle-shaped openings 1020, 1020 are provided between the lens portion 1012 and the plate haptic portion 1014. A plurality of through holes 1022 are provided to facilitate anchoring the perimeter of the plate haptic portion 1014 in the eye. In this embodiment, the lens portion 1012 is located off center along the X axis resulting in the plate haptic portion 1014 being asymmetrical relative to the Y axis.

Figure 17:
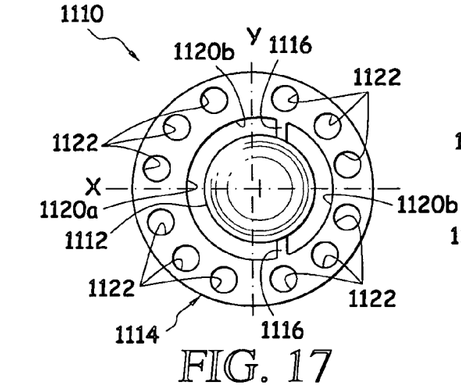
FIG. 17 is a top planar view of a further embodiment of the accommodating intraocular lens according to the present invention.

Another embodiment of the accommodating intraocular lens 1110 according to the present invention is shown in FIG. 17.

The accommodating intraocular lens 1110 includes a round lens portion 1112 connected to a round plate haptic portion 1114 by a pair of flexible or resilient arm portions 1116, 1116. The arm portions 1116, 1116 are both located off axis relative to the Y axis. A pair of half circular-shaped openings 1120a, 1120b are provided between the lens portion 1112 and the plate haptic portion 1114. It is to be noted that the opening 1120a is larger than the opening 1120b. A plurality of through holes 1122 are provided to facilitate anchoring of the perimeter of the plate haptic portion 1114 in the eye.

Figure 18:
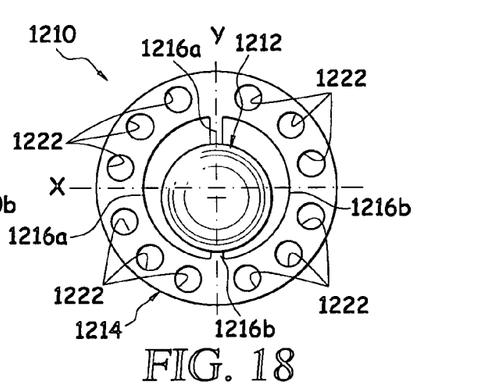
FIG. 18 is a top planar view of a further embodiment of the accommodating intraocular lens according to the present invention.

Another embodiment of the accommodating intraocular lens 1210 according to the present invention is shown in FIG. 18.

The accommodating intraocular lens 1210 includes a round lens portion 1212 connected to a round plate haptic portion 1214 by a pair of flexible or resilient arm portions 1216a and 1216b. It is to be noted that the arm portion 1216a is longer than the arm portion 1216b. A pair of asymmetrical half circular-shaped openings 1220 are provided between the lens portion 1212 and the plate haptic portion 1214. A plurality of through holes 1222 are provided to facilitate anchoring of the perimeter of the plate haptic portion 1214 in the eye.

Figure 19:
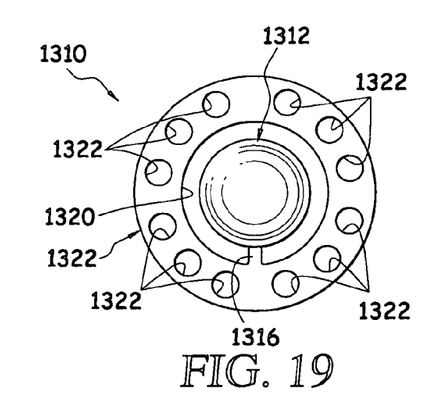
FIG. 19 is a top planar view of a further embodiment of the accommodating intraocular lens according to the present invention.

Another embodiment of the accommodating intraocular lens 1310 according to the present invention is shown in FIG. 19.

The accommodating intraocular lens 1310 includes a round lens portion 1312 connected to a round plate haptic portion 1314 by a single flexible or resilient arm portion 1316. A single circular-shaped opening 1320 is provided to separate the lens portion 1312 from the plate haptic portion 1314. A plurality of through holes 1322 are provided to facilitate anchoring of the perimeter of the plate haptic portion 1314 in the eye.

Figure 20:
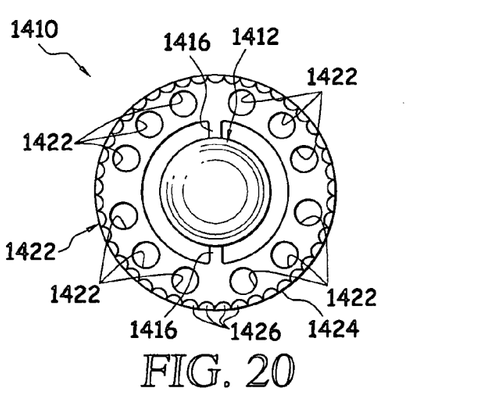
FIG. 20 is a top planar view of a further embodiment of the accommodating intraocular lens according to the present invention.

Another embodiment of the accommodating intraocular lens 1410 according to the present invention is shown in FIG. 20.

The accommodating intraocular lens 1410 includes a round lens portion 1412 connected to a round plate haptic portion 1414 by a pair of flexible or resilient arm portions 1416, 1416. A pair of half circular-shaped openings 1420, 1420 are provided between the lens portion 1412 and the plate haptic portion 1414. A plurality of through holes 1422 are provided to facilitate anchoring of the perimeter of the plate haptic portion 1414 in the eye. In addition, the edge 1424 is provided with scalloped portions 1426 around the perimeter thereof to facilitate the fibrotic fixation process. Alternatively, or in addition, the scallops can be replaced with serrations, notches and/or flaps.

Figure 21:
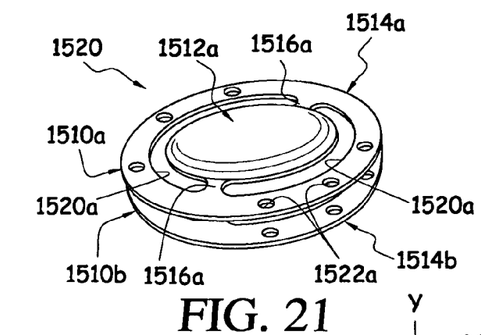
FIG. 21 is a perspective view of an accommodating intraocular lens device according to the present invention having double lens portions.
Figure 22:
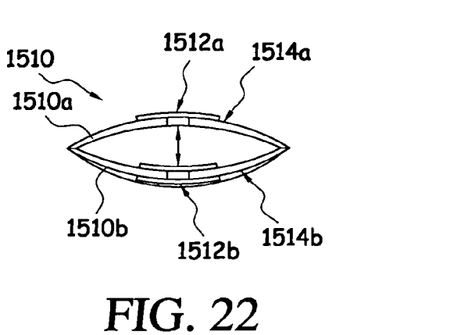
FIG. 22 is a center cross-sectional view of the accommodating intraocular lens shown in FIG. 21.

A double lens embodiment of the accommodating intraocular lens 1510 according to the present invention is shown in FIGS. 21 and 22.

The accommodating lens 1510 includes a front accommodating lens portion 1510a and a back accommodating lens portion 1510b. The lens portion 1510a and the lens portion 1510b are essentially the same configuration except reverse oriented and assembled back-to-back.

The accommodating intraocular lens portion 1510a includes a round lens portion 1512a connected to a round plate haptic portion 1514a by a pair of flexible or resilient arm portions 1516a, 1516a. A pair of half circular-shaped openings 1520a, 1520a are provided between the lens portion 1512a and the plate haptic portion 1514a. A plurality of through holes 1522a are provided to facilitate anchoring of the perimeter of the plate haptic portion 1514a in the eye. The accommodating lens portion 1510b is the same or similarly configured to the accommodating lens portion 1510a. As shown in FIG. 22, the outer edges or perimeter of the lens portion 1510a and 1510b contact or engage each other when implanted in the eye.

A preferred embodiment of the accommodating intraocular lens haptic portion according to the present invention has a length preferably from 8 millimeters to 13 millimeters, a width from 5 to 13 millimeters, and a thickness from 0.05 millimeters to 1 millimeter. The opening distance D is preferably 0.20 to 2.0 millimeters. It is important that the ratio of the radial length of the plate haptic portion relative to the axial thickness of the plate haptic portion is preferably 1.5 to 8 or more, to provide sufficient bowing of the plate haptic portion when stressed inwardly by forces applied by the eye.

LENS OPERATION

The accommodating intraocular lens according to the present invention is configured to bow or flex due to forces applied by the eye to the accommodating intraocular lens, in particular to forces applied to the edge portions of the plate haptic portion.

The accommodating intraocular lens according to the present invention can be located potentially in the anterior chamber and/or posterior chamber of the eye. Preferably the accommodating intraocular lens according to the present invention in located in the posterior chamber capsular bag of the eye after cataract lens removal.

In operation, forces that are exerted on the capsular bag by the zonules of the eye are applied to the accommodating intraocular lens according to the present invention, in particular to the peripheral edges thereof. As forces are applied to the outer edges of the accommodating intraocular lens according to the present invention by the eye, the plate haptic portion begins to bow in an arch generally perpendicular to the flexible or resilient arm portions connecting the lens portion to the plate haptic portion so as to move the lens portion either forward or rearward from a resting position depending on the particular configuration and arrangement. In any event, the accommodating intraocular lens according to the present invention is configured so that the plate haptic portion moves the lens portion during operation.

The operation or functioning of the intraocular lens 10 according to the present invention is shown in FIGS. 23-26.

Figure 23:
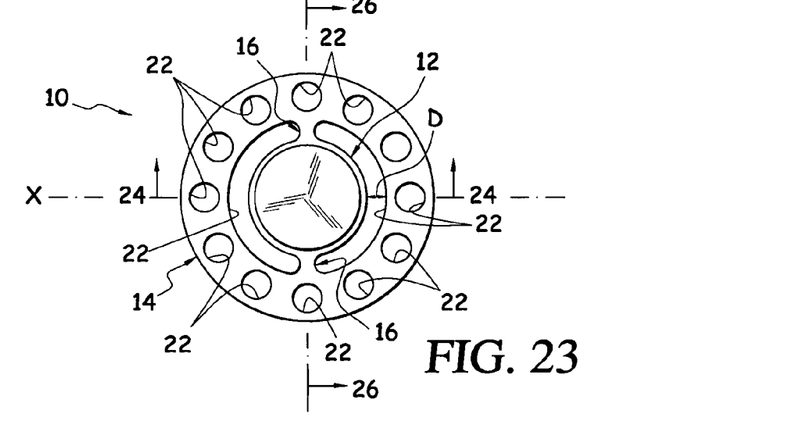
FIG. 23 is a top planar view of the lens shown in FIG. 2 in a resting or unstressed condition.
Figure 24:
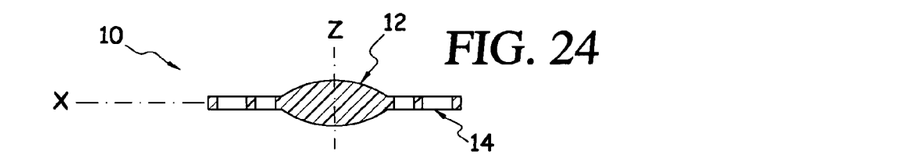
FIG. 24 is a center cross-sectional view of the accommodating intraocular lens, as indicated in FIG. 23.
Figure 25:
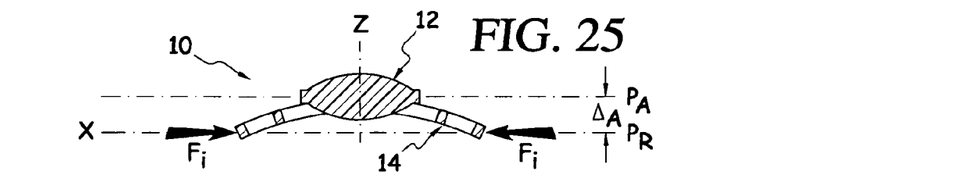
FIG. 25 is a center cross-sectional view of the accommodating intraocular lens shown in FIG. 24 in a stressed condition showing the plate haptic portion bowing and the lens portion moving along the optical axis Z of the eye.
Figure 26:
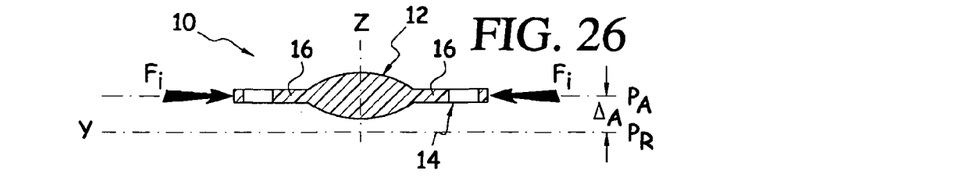
FIG. 26 is a center cross-sectional view of the accommodating intraocular lens as indicated in FIG. 23, along the transverse axis Y.

The accommodating intraocular lens 10 is shown in an unstressed and unbowed condition, as shown in FIGS. 23 and 24. When inwardly directed forces $F_i$ are applied around the perimeter of the plate haptic portion 14, the plate haptic portion 14 begins to bow relative to the X axis as illustrated in FIG. 25, and may furthermore be enhanced by varying hydraulic pressures in the eye. In this manner, the lens portion 12 is moved from a resting position plane $P_R$ to an accommodating plane $P_A$ and traverses a distance $\Delta_A$. However, as illustrated in FIG. 26, the plate haptic portion 14 does not bow or substantially bow along the tranverse axis Y, since the flexible or resilient arm portion 16, 16 reinforce and stiffen the plate haptic portion 14 from bowing along this tranverse axis Y. Thus, the accommodating intraocular lens 10 essentially bows in only a single dimension, and not in two (2) dimensions.

As illustrated in FIG. 25, the outer edges of the lens portion 12 become somewhat separated and exposed from the upper surface of the plate haptic portion 14 due to bowing of the plate haptic portion 14. In this manner, it is possible that the lens portion 12 could potentially extend into or through the pupil of the iris of the eye. However, as illustrated in FIG. 26, the arm portions 16 do not allow the plate haptic portion 14 to bow in the tranverse axis Y, and prevents the lens portion 12 from being exposed and separating from the upper surface of the plate haptic portion 14. Further, the arm portion 16 acts or functions like a pair of bumpers against the back of the iris at the opening of the pupil to prevent the lens portion 12 from entering into or passing through the pupil of the iris of the eye.

I claim:

1. An accommodating intraocular lens device configured to be implanted into an eye, said lens device comprising:
   a single circular-shaped lens optic portion configured to be initially located in a reference plane oriented substantially perpendicular to a central focal axis of the eye when said lens device is implanted within the eye;
   a lens plate haptic portion surrounding said lens optic portion at a predetermined distance by a circular-shaped through hole separating said lens optic portion from said lens plate haptic portion, said lens plate haptic portion configured to bow when forces are applied by the eye inwardly on opposite edges of said plate haptic portion, said plate haptic portion being located in said reference plane; and
   at least one lens connection portion defined by said circular-shaped through hole and configured to connect said lens optic portion to said lens plate haptic portion, said lens plate haptic portion and said lens connection portion configured to move said lens optic portion in and out of said reference plane in a manner to focus the eye when force is applied by the eye inwardly to said opposite edges of said plate haptic portion causing said plate haptic portion to bow.

2. A lens device according to claim 1, wherein said lens connection portion is defined by at least one flexible arm.

3. A lens device according to claim 2, wherein said lens connection portion is defined by a pair of flexible arms located at opposite ends of said lens optic portion.

4. A lens device according to claim 2, wherein said at least one arm extends from an outer edge of said lens optic portion to an inner edge of said lens plate haptic portion.

5. A lens device according to claim 3, wherein said pair of flexible arms are located along a first axis located in said reference plane;

6. A lens device according to claim 5, wherein said pair of flexible arms are located along said first axis located in said reference plane, said first axis being oriented substantially perpendicular to a second axis located in said reference plane along which said force is applied by the eye inwardly on said opposite edges of said lens plate hapric portion.

7. A lens device according to claim 5, wherein said pair of flexible arms is initially located in said reference plane.

8. A lens device according to claim 6, wherein a center of said lens optic portion is located along said second axis.

9. A lens device according to claim 6, wherein a center of said lens optic portion is located off axis relative to said second axis.

10. A lens device according to claim 8, wherein said lens optic portion is centered between said opposite edges of said lens plate haptic portion.

11. A lens device according to claim 8, wherein said lens optic portion is not centered between said opposite edges of said lens plate haptic portion.

12. A lens device according to claim 1, wherein said lens connection portion is configured to prevent bowing of said lens optic portion when said lens plate haptic portion is being bowed.

13. A lens device according to claim 1, wherein said lens connection portion is defined by at least one flexible arm connecting said lens optic portion to said lens plate haptic portion.

14. A lens device according to claim 13, wherein said at least one flexible arm is initially located in said reference plane.

15. A lens device according to claim 1, wherein said lens plate haptic portion is provided with at least one peripheral through hole configured to facilitate anchoring of an edge of said lens plate haptic portion within the eye.

16. A lens device according to claim 1, wherein at least a portion of an edge of said lens plate haptic portion is provided with an edge finish configured to facilitate anchoring of said edge of said lens plate haptic portion within the eye.

17. A lens device according to claim 16, wherein said edge finish is at least one selected from the group consisting of scallops, serrations, notches and flaps.

18. A lens device according to claim 1, wherein said lens optic portion is centered between said opposite edges of said lens plate haptic portion.

19. A lens device according to claim 1, wherein said lens optic portion is not centered between said opposite edges of said lens plate haptic portion.

20. A lens device according to claim 1, wherein said lens optic portion is centered between said opposite edges of said lens plate haptic portion.

21. A lens device according to claim 1, wherein said lens optic portion is not centered between said opposite edges of said lens plate haptic portion.

22. A lens device according to claim 1, wherein said lens device is made from at least one material selected from the group consisting of silicone, collagen based polymer, polymethyl methacrylate, acrylic polymer, polyamide, polyester, and polysulfane.

23. A lens device according to claim 1, wherein said lens device is configured to bow only relative to a first axis.

24. A lens device according to claim 23, wherein said lens optic device is configured not to bow relative to a second axis oriented transverse relative to said first axis, and said lens connection portion is defined by a pair of flexible arms connecting said lens optic portion to said lens plate haptic portion and aligned along said second axis.

25. An accommodating intraocular lens device configured to be implanted into a capsular bag of an eye after cataract lens removal, said lens device comprising:
   a single circular-shaped lens optic portion configured to be initially located in a reference plane oriented substantially perpendicular to a central focal axis of the eye when said lens device is implanted within the eye;

a lens plate haptic portion surrounding said lens optic portion with at least one circular-shaped through hole separating and spacing apart said lens optic portion a fixed predetermined distance from said lens plate haptic portion, said lens plate haptic portion configured to bow when force is applied by the eye onto said lens plate haptic portion, said lens plate haptic portion being located in said reference plane, said lens optic portion and said lens plate haptic being configured to fit within the capsular bag of the eye after natural lens removal; and at least one flexible lens connection portion defined by said circular-shaped through hole and configured to connect said lens optic portion to said lens plate haptic portion, said lens plate haptic portion and said lens connection portion configured to move said lens optic portion in and out of said reference plane in a manner to focus the eye when force is applied by the eye onto said lens plate haptic portion causing said lens plate haptic portion to bow, said lens connection portion being defined by a pair of flexible arms connecting said lens optic portion to said lens plate haptic portion at opposite ends of said lens optic portion along a first axis located in said reference plane oriented substantially perpendicular to a second axis located in said reference plane along which said force is applied by the eye inwardly to opposite edges of said plate haptic portion.

* * * * *